United States Patent [19]

Ito et al.

[11] Patent Number: 4,762,948
[45] Date of Patent: Aug. 9, 1988

[54] PROCESS FOR PREPARING OPTICALLY ACTIVE ARYLACETIC ACID DERIVATIVE

[75] Inventors: Yoshihiko Ito; Tamio Hayashi, both of Kyoto; Norio Kawamura, Yao; Ichiki Takemoto, Toyonaka, all of Japan

[73] Assignee: Sumitomo Chemical Company, Limited, Osaka, Japan

[21] Appl. No.: 71,306

[22] Filed: Jul. 9, 1987

[30] Foreign Application Priority Data

Jan. 21, 1987 [JP] Japan .................. 62-013248

[51] Int. Cl.⁴ .................. C07C 57/30; C07C 63/36
[52] U.S. Cl. .................. 562/496; 562/490
[58] Field of Search .................. 562/496, 490

[56] References Cited

U.S. PATENT DOCUMENTS

| 4,119,652 | 10/1978 | Knowles | 562/496 |
| 4,198,510 | 4/1980 | Shioiri et al. | 562/496 |
| 4,409,397 | 10/1983 | Paxson . | |
| 4,440,936 | 4/1984 | Riley | 562/496 |

FOREIGN PATENT DOCUMENTS 4059238 12/1979 Japan .................. 562/496

*Primary Examiner*—Paul J. Killos
*Attorney, Agent, or Firm*—Birch, Stewart, Kolasch & Birch

[57] ABSTRACT

An optically active arylacetic acid derivative of the formula:

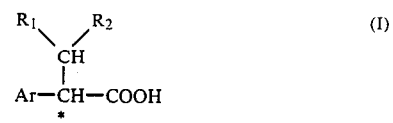

(I)

wherein $R_1$ and $R_2$ are the same or different and are each an hydrogen atom, a lower alkyl group or a phenyl group; and Ar is a group of the formula:

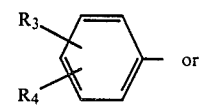

or a group of the formula:

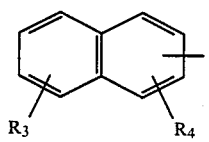

wherein $R_3$ and $R_4$ are the same or different and are each a hydrogen atom, a halogen atom, a lower alkyl group, a lower alkoxy group, a difluoromethoxy group, a trifluoromethyl group or a phenyl group is prepared in good conversion and optical yield by asymmetrically reducing an ethylenically unsaturated compound of the formula:

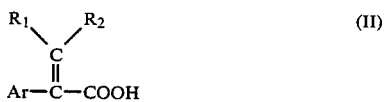

(II)

wherein $R_1$, and $R_2$ and Ar are the same as defined above with hydrogen in the presence of a metal catalyst modified with a ligand selected from the group consisting of a specific optically active metallocenyl phosphine derivative and a specific optically active binaphthyl derivative.

17 Claims, No Drawings

PROCESS FOR PREPARING OPTICALLY ACTIVE ARYLACETIC ACID DERIVATIVE

BACKGROUND OF THE INVENTION

1. Field of the Invention

The present invention relates to a process for preparing an optically active arylacetic acid derivative. More particularly, the present invention relates to a process for preparing an optically active arylacetic acid derivative useful as an intermediate for the preparation of medicines and agricultural chemicals.

2. Description of the Prior Art

It is known from U.S. Pat. No. 4,409,397 to use a catalyst of the formula:

$$LM(olefin)_2{}^+X^- \quad (V)$$

wherein M is a rhodium atom, a ruthenium atom or an iridium atom, L is an asymmetric ligand of ferrocenyl phosphine or pyridinyl phosphine, (olefin)$_2$ represents 2,5-norbornadiene or 1,5-cyclooctadiene, and X is ClO$_4$, BF$_4$ or PF$_6$ in the preparation of optically active phenylacetic acid by asymmetric reduction with hydrogen. As ferrocenyl phosphine, disclosed in this patent is an optically active ferrocenyl phosphine of the formula:

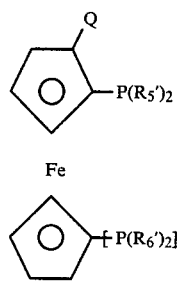

(VI)

wherein R$_5'$ and R$_6'$ are each a lower alkyl group, a C$_5$–C$_8$ cycloalkyl group, a phenyl group or a C$_5$–C$_6$ heterocyclic group, Q is a lower alkyl group, an alkenyl group or a group of the formula:

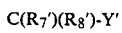

$$C(R_7')(R_8')-Y'$$

wherein R$_7'$ and R$_8'$ are each a hydrogen atom, a lower alkyl group or an aryl group or together form a cycloalkyl group, and Y' is an hydrogen atom, a hydroxyl group, an acyloxy group or a group of the formula:

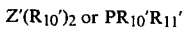

$$Z'(R_{10}')_2 \text{ or } PR_{10}'R_{11}'$$

wherein Z' is N, P, As or Sb, R$_{10}'$ and R$_{11}'$ are each a hydrogen atom or an alkyl group or (R$_{10}'$)$_2$ forms a heterocyclic group containing N or P in Z' and optionally additional N or O; and n is 0 (zero) or 1 (one).

The process for preparing the optically active phenylacetic acid derivative by using a metal catalyst modified with such optically active ferrocenyl phosphine compounds is not industrially satisfactory since it cannot necessarily produce the desired compound in a high optical yield and conversion.

SUMMARY OF THE INVENTION

One object of the present invention is to provide a process for preparing an optically active arylacetic acid derivative in a high yield and high conversion.

Another object of the present invention is to provide a process for preparing an optically active arylacetic acid in the presence of a metal catalyst modified with an optically active metallocenyl phosphine derivative or an optically active binaphthyl derivative.

These and other objects of the present invention are achieved by a process for preparing an optically active arylacetic acid derivative of the formula:

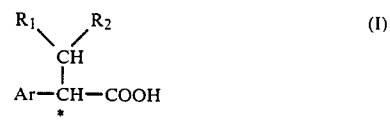

(I)

wherein R$_1$ and R$_2$ are the same or different and are a hydrogen atom, a lower alkyl group or a phenyl group; and Ar is a group of the formula:

or a group of the formula:

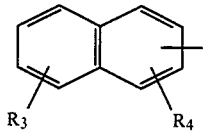

wherein R$_3$ and are R$_4$ are the same or different and each a hydrogen atom, a halogen atom, a lower alkyl group, a lower alkoxy group, a difluoromethoxy group, a trifluoromethyl group or a phenyl group, which comprises asymmetrically reducing an ethylenically unsaturated compound of the formula:

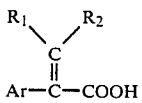

(II)

wherein R$_1$, R$_2$ and Ar are the same as defined above with hydrogen in the presence of a metal catalyst modified with a ligand selected from the group consisting of:

an optically active metallocenyl phosphine derivative of the formula:

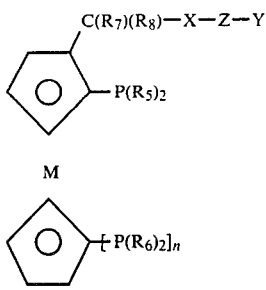

(III)

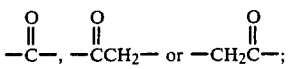

wherein $R_5$ and $R_6$ are the same or different and are each a lower alkyl group, a $C_5$–$C_8$ cycloalkyl group, an aryl group or a $C_5$–$C_6$ heterocyclic group; $R_7$ and $R_8$ are the same or different and are each a hydrogen atom or a lower alkyl group; X is a methylene group, an oxygen atom or a group of the formula: -$NR_9$ wherein $R_9$ is an hydrogen atom or a lower alkyl group; Z is an alkylene group, or a group of the formula:

$$-\overset{O}{\underset{\|}{C}}-, \quad -\overset{O}{\underset{\|}{C}}CH_2- \quad \text{or} \quad -CH_2\overset{O}{\underset{\|}{C}}-;$$

Y is a group of the formula: -$OR_{10}$ or

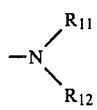

wherein $R_{10}$, $R_{11}$ and $R_{12}$ are the same or different and are each a hydrogen atom or a lower alkyl group or $R_{11}$ and $R_{12}$ together form a heterocyclic group containing the nitrogen atom to which they are bonded and optionally an additional oxygen or nitrogen atom; M is Fe, Ru or Os; and n is 0 (zero) or 1 (one) and an optically active binaphthyl derivative of the formula:

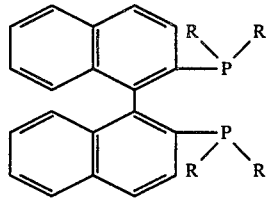

(IV)

wherein R is a phenyl group, a p-tolyl group, a p-methoxyphenyl group or a cyclohexyl group.

DETAILED DESCRIPTION OF THE INVENTION

In the context of the present invention, "halogen" is intended to mean fluorine, chlorine, bromine and iodine, the terms "lower alkyl" or the "lower alkoxy" are intended to include those having 1 to 6 carbon atoms such as methyl, ethyl, propyl, isopropyl, butyl, sec-butyl, tert-butyl, isobutyl, isoamyl, pentyl, hexyl, or methoxy, ethoxy, propoxy, isopropoxy, butoxy, isobutoxy, pentyloxy or hexyloxy, the "aryl group" is intended to encompass phenyl, p-tolyl, p-methoxyphenyl, etc., the "alkylene group" is intended to mean a divalent lower alkenyl group having 1 to 6 carbon atoms such as methylene, ethylene, trimethylene, tetramethylene, pentamethylene, hexamethylene, ethylethylene, methyltet- ramethylene, and the heterocyclic group formed by $R_{11}$ and $R_{12}$ is intended to mean pyrrolidinyl, piperidino, morpholino, piperazyl, hexahydro-1H-azepinyl, 4-methylpiperazyl, etc.

As the ethylenically unsaturated compound (II) used in the process of the present invention, there are exemplified 2-phenyl-3-methylcrotonic acid, 2-(4-chlorophenyl)-3-methylcrotonic acid, 2-(4-methoxyphenyl)-3-methylcrotonic acid, 2-(4-difluoromethoxyphenyl)-3-methylcrotonic acid, 2-(4-isobutylphenyl)acrylic acid, 2-(6-methoxynaphthyl-2)acrylic acid, 2-phenylacrylic acid, 2-phenyl-3-ethylpentenoic acid, 2-(4-chlorophenyl)-3-ethylpentenoic acid, 2-(2-naphthyl)-3-methylcrotonic acid, 2-phenyl-3-methylcinnamic acid, 2-phenyl-3-methyl-2-pentenoic acid, etc. These and other compounds of the formula (II) can be prepared by an analogous process to that described in U.S. Pat. No. 4,409,397, the disclosure of which is hereby incorporated by reference.

Among the optically active metallocenyl phosphine derivatives, a derivative (III) wherein the metal atom M is an iron atom is preferred. Preferably, $R_5$ and $R_6$ are independently a t-butyl group, a cyclohexyl group or a phenyl group; $R_7$ is a hydrogen atom; $R_8$ is a methyl group; X is NMe; Z is a methylene group, an ethylene group, a trimethylene group, a tetramethylene group or a carbonyl group; Y is —$N(R_{11})(R_{12})$ wherein $R_{11}$ and $R_{12}$ are independently a lower alkyl group.

According to one embodiment of the present invention, a metal catalyst modified with such metallocenyl phosphine derivative (III) is used. Preferred examples of the metal component in the catalyst are transition metals such as rhodium, iridium and ruthenium.

Specific examples of the metal catalyst are as follows:

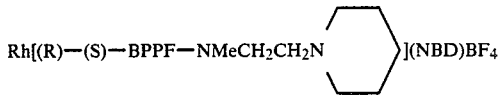

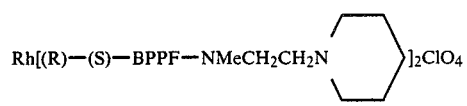

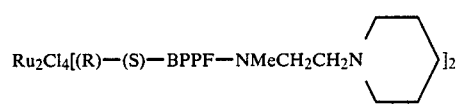

Rh[(R)-(S)-BPPF-NMeCH$_2$CH$_2$NEt$_2$](NBD)BF$_4$,
Rh[(R)-(S)-BPPF-NMeCH$_2$CH$_2$NEt$_2$]$_2$ClO$_4$,
Ru$_2$Cl$_4$[(R)-(S)-BPPF-NMeCH$_2$CH$_2$NEt$_2$]$_2$
wherein

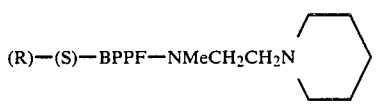

and (R)-(S)-BPPF-NMeCH$_2$-CH$_2$NEt$_2$ represent (R)-N-methyl-[2-(1-piperidine)ethyl]-1-[(S)-1′,2-bis(diphenylphosphino)-ferrocenyl]ethylamine and (R)-N-methyl-[2-(diethylamino)ethyl]-1-[(S)-1′,2-bis(diphenylphosphino)ferrocenyl]ethylamine, respectively, and NBD represents 2,5-norbornadiene.

The modified metal catalyst can be prepared by a per se conventional process according to those described in Bull. Chem. Soc. Jpn., 53, 1138 (1980), Acc. Chem. Res., 15, 395, (1982), J. Am. Chem. Soc., 99, 6262 (1977) and J. Am. Chem. Soc., 108, 6405 (1986).

For example, (R)-(S)-BPPF-NMeCH$_2$CH$_2$NEt$_2$ is prepared by reacting (R)-(S)-BPPF-OCOMe with HNMeCH$_2$CH$_2$NEt$_2$ according to the following reaction formula:

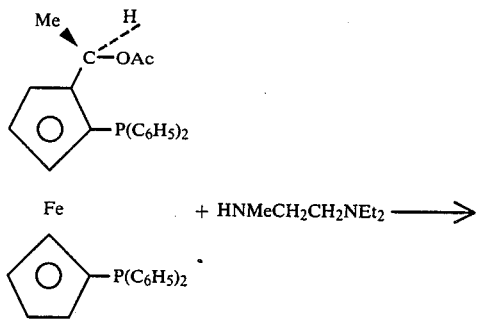

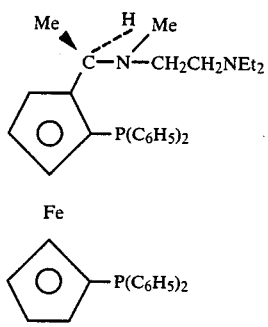

Rh[(R)-(S)-BPPF-NMeCH$_2$CH$_2$NEt$_2$](NBD)BF$_4$ is prepared by reacting Rh(NBD)2BF$_4$ with (R)-(S)-BPPF-NMeCH$_2$CH$_2$NEt$_2$ in methanol to replace NBD with (R)-(S)-BPPF-NMeCH$_2$CH$_2$NEt$_2$.

Specific examples of the metal catalyst modified with the optically active binaphthyl derivative (IV) are
Rh(BINAP)(COD)BF$_4$,
Rh(BINAP)$_2$ClO$_4$, and
Ru$_2$Cl$_4$(BINAP)$_2$ wherein BINAP represents 2,2'-bis(diphenylphosphino)-1,1'-binaphthyl and COD represents 1,5-cyclooctadiene. These catalysts are prepared by a per se conventional process according to those described in Tetrahedron, 40, 1245 (1984), J. Chem. Soc., Chem. Commun., 922 (1985), Japanese Patent Kokai Publication Nos. 61587/1985 and J. Org. Chem., 51, 629 (1986). For example, Rh(BINAP)(COD)BF$_4$ is prepared by reacting Rh$_2$(COD)$_2$Cl$_2$ with BINAP in methanol in the presence of AgBF$_4$ to replace COD with BINAP.

In the process according to the present invention, the catalyst is used in an amount of 0.001 to 10% by mole, preferably 0.01 to 1% by mole, based on the amount of the ethylenically unsaturated compound (II).

Usually, the reaction of the present invention is carried out in a solvent. Specific examples of the solvent are organic solvents such as methanol, ethanol, isopropanol, butanol, methyl acetate, benzene, toluene, xylene, tetrahydrofuran, and water or mixtures thereof. Among them, methanol and ethanol are preferred. The solvent is used in an amount of 1 to 500 parts by weight, preferably 10 to 200 parts by weight, per part by weight of the ethylenically unsaturated compound (II).

The pressure of hydrogen to be supplied to the reaction system is usually from atmospheric pressure to 500 kg/cm$^2$, preferably from 10 to 150 kg/cm$^2$.

The reaction temperature is usually from 0° to 150° C., preferably from room temperature to 150° C.

The reaction time is not critical in the present invention and is usually from 1 to 90 hours.

To the reaction system, a tertiary amine such as triethylamine and tri-n-propylamine may be added in an amount of 0.1 to 100 moles, preferably 1 to 20 moles per mole of the catalyst.

According to the process of the present invention, the optically active arylacetic acid derivative (I) is prepared in good conversion and good optical yield. By changing the configuration of the modifying compound of the metal catalyst, the configuration of the produce arylacetic acid derivative (I) is controlled.

PREFERRED EMBODIMENTS OF THE INVENTION

Practically and presently preferred embodiments of the present invention are shown in the following examples.

EXAMPLE 1

Rh$_2$(NBD)$_2$Cl$_2$ (1.2 mg, 0.0025 mmol), AgBF$_4$ (1.0 mg, 0.005 mmol),

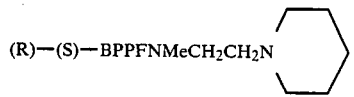

(4.5 mg, 0.00625 mmol) and triethylamine (5.1 mg, 0.05 mmol) were dissolved in methanol (7.5 ml) in a 35 ml autoclave. To the resulting solution, 2-(4-chlorophenyl)-3-methylcrotonic acid (211 mg, 1 mmol) was added and dissolved. After the interior space of the autoclave was replaced with hydrogen gas, hydrogen gas was injected to pressurize the autoclave to 50 kg/cm$^2$, and the solution was stirred for 20 hours at room temperature.

After hydrogen gas was purged, methanol was evaporated off. The residual mixture was extracted with an alkali, precipitated with an acid and extracted with ether followed by concentration to obtain (S)-2-(4-chlorophenyl)-3-methylbutyric acid (211.8 mg).

| | |
|---|---|
| Conversion: | 100% |
| Selectivity: | >98% |
| Optical yield | 93.8% (+isomer) |

Conversion, selectivity and optical yield were calculated from the results of liquid chromatography using an optically active column and an angle of rotation.

EXAMPLE 2

Rh(NBD)$_2$BF$_4$ (1.9 mg, 0.005 mmol) and (R)-(S)-BPPF-NMeCH$_2$CH$_2$NEt$_2$ (4.5 mg, 0.00625 mmol) were dissolved in methanol (7.5 ml) in a 35 ml autoclave. To the resulting solution, 2-(4-chlorophenyl)-3-methylcrotonic acid (211 mg) was added and dissolved. After the interior space of the autoclave was replaced with hydrogen gas, hydrogen gas was injected to pressurize the autoclave to 50 kg/cm², and the solution was stirred for 4 hours at 80° C.

After the autoclave was cooled and hydrogen gas was purged, methanol was evaporated off. The residual mixture was extracted with an alkali, precipitated with an acid and extracted with ether followed by concentration to obtain (S)-2-(4-chlorophenyl)-3-methylbutyric acid (213 mg).

| Conversion: | 100% |
| Selectivity: | >98% |
| Optical yield | 85.4% (+isomer) |

EXAMPLES 3-11

In the same manner as in Example 2 but using an optically active ferrocenyl phosphine derivative shown in Table 1 in place of (R)-(S)-BPPF-NMeCH₂CH₂NEt₂, the reaction and post-treatment were carried out to obtain (S)-2-(4-chlorophenyl)-3-methylbutyric acid. The results are shown in Table 1.

TABLE 1

| Example No. | Ferrocenylphosphine derivative (R)—(S)—BPPF—W | Conversion (%) | Selectivity (%) | Configuration | Optical yield (%) |
|---|---|---|---|---|---|
| 3 | (R)—(S)—BPPF—NMeCH$_2$CH$_2$NMe$_2$ | 100 | >98 | S(+) | 66.7 |
| 4 | (R)—(S)—BPPF—NMeCH$_2$CH$_2$N(i-Pr)$_2$ | 100 | >98 | S(+) | 75.2 |
| 5 | (R)—(S)—BPPF—NMeCH$_2$CH$_2$N(n-Bu)$_2$ | 100 | >98 | S(+) | 77.9 |
| 6 | (R)—(S)—BPPF—NMeCH$_2$CH$_2$N(piperidinyl) | 100 | >98 | S(+) | 70.6 |
| 7 | (R)—(S)—BPPF—NMeCH$_2$CH$_2$N(pyrrolidinyl) | 100 | >98 | S(+) | 66.8 |
| 8 | (R)—(S)—BPPF—NMeCH$_2$CH$_2$N(hexamethyleneimino) | 100 | >98 | S(+) | 84.9 |
| 9 | (R)—(S)—BPPF—NMeCH$_2$CH$_2$N(4-Me-piperazinyl) NMe | 100 | >98 | S(+) | 42.3 |
| 10 | (R)—(S)—BPPF—NMeCH$_2$CH$_2$CH$_2$NEt$_2$ | 100 | >98 | S(+) | 74.7 |
| 11 | (S)—(R)—BPPF—NMeCH$_2$CH$_2$NMe$_2$ | 100 | >98 | R(−) | 66.7 |

(R)-(S)-BPPF-NMeCH₂CH₂Am has the chemical structure of the formula:

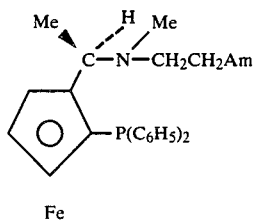

wherein Am is NEt₂ or

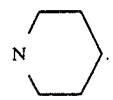

(R)-(S)-BPPF-W has a chemical structure of the formula:

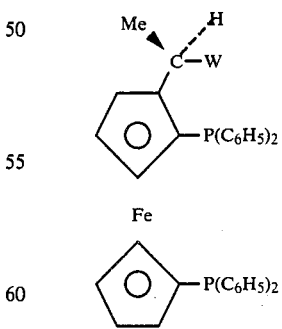

EXAMPLES 12 and 13

In the same manner as in Example 2 but proceeding the reaction under conditions as specified in Table 2, the reaction and post-treatment were carried out. The results are also shown in Table 2.

TABLE 2

| Example No. | 12 | 13 |
|---|---|---|
| Hydrogen pressure (kg/cm²) | 10 | 50 |
| Reaction temp. (°C.) | 50 | 20 |
| Reaction time (hrs) | 4 | 20 |
| Conversion (%) | 99 | 96 |
| Selectivity (%) | >98 | >98 |
| Configuration | S(+) | S(+) |
| Optical yield (%) | 85.0 | 80.7 |

EXAMPLE 14

Rh(COD)$_2$Cl$_2$ (1.2 mg, 0.0025 mmol), AgBF$_4$ (1.0 mg, 0.005 mmol), (R)-(S)-BPPF-NMeCH$_2$CH$_2$NEt$_2$ (4.5 mg, 0.00625 mmol) and triethylamine (5.1 mg, 0.05 mmol) were dissolved in ethanol (7.5 ml) in the same autoclave as used in Example 1. To the resulting solution, 2-(4-chlorophenyl)-3-methylcrotonic acid (211 mg) was added and dissolved. After the interior space of the autoclave was replaced with hydrogen gas, hydrogen gas was injected to pressurize the autoclave to 50 kg/cm², and the solution was stirred for 4 hours at 80° C.

After the autoclave was cooled and hydrogen gas was purged, ethanol was evaporated off. The residual mixture was extracted with alkali, precipitated with an acid and extracted with ether followed by concentration to obtain S-2-(4-chlorophenyl)-3-methylbutyric acid (213 mg).

| Conversion: | 100% |
|---|---|
| Selectivity: | >98% |
| Optical yield | 89.0% (+isomer) |

EXAMPLE 15

Rh(COD)$_2$Cl$_2$ (1.2 mg, 0.0025 mmol), AgBF$_4$ (1.0 mg, 0.005 mmol), (S)-(R)-BPPF-NMéCH$_2$CH$_2$NEt$_2$ (4.5 mg, 0.00625 mmol) and triethylamine (5.1 mg, 0.05 mmol) were dissolved in methanol (7.5 ml) in the same autoclave as used in Example 1. To the resulting solution, 2-phenylacrylic acid (148 mg, 1 mmol) was added and dissolved. After the interior space of the autoclave was replaced with hydrogen gas, hydrogen gas was injected to pressurize the autoclave to 50 kg/cm², and the solution was stirred for 16 hours at room temperature.

After hydrogen gas was purged, methanol was evaporated off. The residual mixture was extracted with alkali, precipitated with an acid and extracted with ether followed by concentration to obtain S-2-phenyl-propionic acid (149.4 mg).

| Conversion: | 100% |
|---|---|
| Selectivity: | >98% |
| Optical yield | 80.7% (+isomer) |

EXAMPLE 16

Rh$_2$(NBD)$_2$Cl$_2$ (1.2 mg, 0.0025 mmol), AgBF$_4$ (1.0 mg, 0.005 mmol),

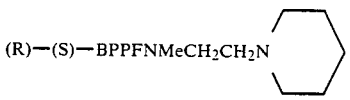

(4.5 mg, 0.00625 mmol) and triethylamine (5.1 mg, 0.05 mmol) were dissolved in methanol (7.5 ml) in a 35 ml autoclave. To the resulting solution, 2-phenyl-3-methylcrotonic acid (176 mg, 1 mmol) was added and dissolved. After the interior space of the autoclave was replaced with hydrogen gas, hydrogen gas was injected to pressurize the autoclave to 50 kg/cm², and the solution was stirred for 20 hours at room temperature.

After hydrogen gas was purged, methanol was evaporated off. The residual mixture was extracted with an alkali, precipitated with an acid and extracted with ether followed by concentration to obtain (S)-2-phenyl-3-methylbutyric acid (177 mg).

| Conversion: | 100% |
|---|---|
| Selectivity: | >98% |
| Optical yield | 95.8% (+isomer) |

EXAMPLE 17

Rh$_2$(NBD)$_2$Cl$_2$ (1.2 mg, 0.0025 mmol), AgBF$_4$ (1.0 mg, 0.005 mmol),

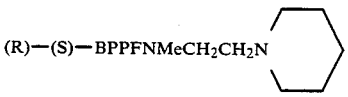

(4.5 mg, 0.00625 mmol) and triethylamine (5.1 mg, 0.05 mmol) were dissolved in methanol (7.5 ml) in a 35 ml autoclave. To the resulting solution, 2-(4-methoxyphenyl)-3-methylcrotonic acid (206 mg, 1 mmol) was added and dissolved. After the interior space of the autoclave was replaced with hydrogen gas, hydrogen gas was injected to pressurize the autoclave to 50 kg/cm², and the solution was stirred for 20 hours at room temperature.

After hydrogen gas was purged, methanol was evaporated off. The residual mixture was extracted with an alkali, precipitated with an acid and extracted with ether followed by concentration to obtain (S)-2-(4-methoxyphenyl)-3-methylbutyric acid (205.5 mg).

| Conversion: | 100% |
|---|---|
| Selectivity: | >98% |
| Optical yield | 91.9% (+isomer) |

EXAMPLE 18

Rh$_2$(NBD)$_2$Cl$_2$ (1.2 mg, 0.0025 mmol), AgBF$_4$ (1.0 mg, 0.005 mmol),

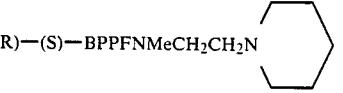

(4.5 mg, 0.00625 mmol) and triethylamine (5.1 mg, 0.05 mmol) were dissolved in methanol (7.5 ml) in a 35 ml autoclave. To the resulting solution, 2-(2-naphthyl)-3-methylcrotonic acid (226 mg, 1 mmol) was added and dissolved. After the interior space of the autoclave was replaced with hydrogen gas, hydrogen gas was injected to pressurize the autoclave to 50 kg/cm$^2$, and the solution was stirred for 6 hours at 50° C.

After the autoclave was cooled and hydrogen gas was purged, methanol was evaporated off. The residual mixture was extracted with an alkali, precipitated with an acid and extracted with ether followed by concentration to obtain (S)-2-(2-naphthyl)-3-methylbutyric acid (226 mg).

| Conversion: | 100% |
| --- | --- |
| Selectivity: | >98% |
| Optical yield | 91.3% (+isomer) |

EXAMPLE 19

Rh$_2$(NBD)$_2$Cl$_2$ (1.2 mg, 0.0025 mmol), AgBF$_4$ (1.0 mg, 0.005 mmol),

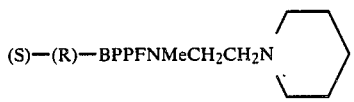

(4.5 mg, 0.00625 mmol) and triethylamine (5.1 mg, 0.05 mmol) were dissolved in methanol (7.5 ml) in a 35 ml autoclave. To the resulting solution, 2-phenyl-3-methylcinnamic acid (238.3 mg, 1 mmol) was added and dissolved. After the interior space of the autoclave was replaced with hydrogen gas, hydrogen gas was injected to pressurize the autoclave to 100 kg/cm$^2$, and the solution was stirred for 50 hours at room temperature.

After hydrogen gas was purged, methanol was evaporated off. The residual mixture was extracted with an alkali, precipitated with an acid and extracted with ether followed by concentration to obtain erythro-2,3-diphenylbutyric acid (240.2 mg).

| Conversion: | 100% |
| --- | --- |
| Selectivity: | >98% |
| Optical yield | 83.2% (−isomer) |

EXAMPLE 20

Rh$_2$(NBD)$_2$Cl$_2$ (1.2 mg, 0.0025 mmol), AgBF$_4$ (1.0 mg, 0.005 mmol),

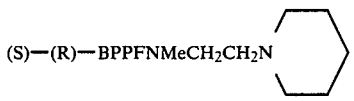

(4.5 mg, 0.00625 mmol) and triethylamine (3.5 mg, 0.025 mmol) were dissolved in methanol (7.5 ml) in a 35 ml autoclave. To the resulting solution, (E)-2-phenyl-3-methyl-2-pentenoic acid (95.1 mg, 0.5 mmol) was added and dissolved. After the interior space of the autoclave was replaced with hydrogen gas, hydrogen gas was injected to pressurize the autoclave to 100 kg/cm$^2$, and the solution was stirred for 90 hours at room temperature.

After hydrogen gas was purged, methanol was evaporated off. The residual mixture was extracted with an alkali, precipitated with an acid and extracted with ether followed by concentration to obtain erythro-2-phenyl-3-methylpentanoic acid (96.0 mg).

| Conversion: | 100% |
| --- | --- |
| Selectivity: | >98% |
| Optical yield | 90.1% (−isomer) |

EXAMPLE 21

Rh$_2$(NBD)$_2$Cl$_2$ (1.2 mg, 0.0025 mmol), AgBF$_4$ (1.0 mg, 0.005 mmol)

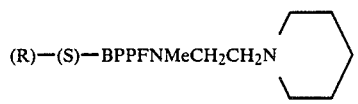

(4.5 mg, 0.00625 mmol) and triethylamine (5.1 mg, 0.05 mmol) were dissolved in a mixed solvent of methanol and tetrahydrofuran (1:4) (7.5 ml) in a 35 ml autoclave. To the resulting solution, 2-phenyl-3-methylcrotonic acid (176 mg, 1 mmol) was added and dissolved. After the interior space of the autoclave was replaced with hydrogen gas, hydrogen gas was injected to pressurize the autoclave to 50 kg/cm$^2$, and the solution was stirred for 20 hours at room temperature.

After hydrogen gas was purged, the solvents were evaporated off. The residual mixture was extracted with an alkali, precipitated with an acid and extracted with ether followed by concentration to obtain (S)-2-phenyl-3-methylbutyric acid (177 mg).

| Conversion: | 100% |
| --- | --- |
| Selectivity: | >98% |
| Optical yield | 97.6% (+isomer) |

EXAMPLE 22

Rh$_2$(NBD)$_2$Cl$_2$ (1.2 mg, 0.0025 mmol), AgBF$_4$ (1.0 mg, 0.005 mmol),

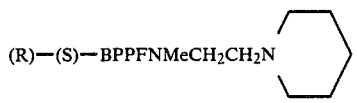

(4.5 mg, 0.00625 mmol) and triethylamine (5.1 mg, 0.05 mmol) were dissolved in a mixed solvent of methanol and tetrahydrofuran (1:4) (7.5 ml) in a 35 ml autoclave. To the resulting solution, 2-(4-chlorophenyl)-3-methylcrotonic acid (211 mg, 1 mmol) was added and dissolved. After the interior space of the autoclave was replaced with hydrogen gas, hydrogen gas was injected to pressurize the autoclave to 50 kg/cm$^2$, and the solution was stirred for 40 hours at room temperature.

After hydrogen gas was purged, the solvents were evaporated off. The residual mixture was extracted with an alkali, precipitated with an acid and extracted with ether followed by concentration to obtain (S)-2-(4-chlorophenyl)-3-methylbutyric acid (213 mg).

| Conversion: | 100% |
| --- | --- |
| Selectivity: | >98% |

| -continued | |
|---|---|
| Optical yield | 97.4% (+isomer) |

EXAMPLE 23

Rh$_2$(NBD)$_2$Cl$_2$ (1.2 mg, 0.0025 mmol), AgBF$_4$ (1.0 mg, 0.005 mmol),

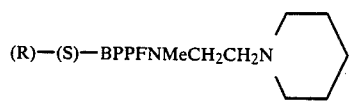

(4.5 mg, 0.00625 mmol) and triethylamine (5.1 mg, 0.05 mmol) were dissolved in a mixed solvent of methanol and tetrahydrofuran (1:4) (7.5 ml) in a 35 ml autoclave. To the resulting solution, 2-(2-naphthyl)-3-methylcrotonic acid (226 mg, 1 mmol) was added and dissolved. After the interior space of the autoclave was replaced with hydrogen gas, hydrogen gas was injected to pressurize the autoclave to 50 kg/cm$^2$, and the solution was stirred for 65 hours at room temperature.

After hydrogen gas was purged, the solvents were evaporated off. The residual mixture was extracted with an alkali, precipitated with an acid and extracted with ether followed by concentration to obtain (S)-2-(2-naphthyl)-3-methylbutyric acid (226 mg).

| Conversion: | 100% |
|---|---|
| Selectivity: | >98% |
| Optical yield | 96.7% (+isomer) |

COMPARATIVE EXAMPLE 1

According to the process described in U.S. Pat. No. 4,409,397, Rh(NBD)$_2$BF$_4$ (1.9 mg, 0.005 mmol), (R)-(S)-BPPF-NMe$_2$ (3.9 mg, 0.00625 mmol) and triethylamine (2.5 mg, 0.025 mmol) were dissolved in methanol (7.5 ml) in a 35 ml autoclave. To the resulting solution, 2-(4-chlorophenyl)-3-methylcrotonic acid (211 mg, 1 mmol) was added and dissolved. After the interior space of the autoclave was replaced with hydrogen gas, hydrogen gas was injected to pressurize the autoclave to 50 kg/cm$^2$. Under the same pressure, the solution was stirred for 4 hours at 80° C.

After the reaction was completed, the reaction mixture was treated in the same manner as in Example 1 to obtain S-2-(4-chlorophenyl)-3-methylbutyric acid (212 mg).

| Conversion: | 100% |
|---|---|
| Selectivity: | >98% |
| Optical yield | 15.8% (+isomer) |

(R)-(S)-BPPF-NMe$_2$ has the chemical structure of the formula:

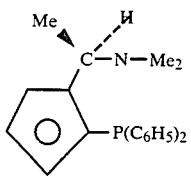

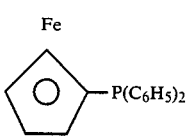

COMPARATIVE EXAMPLE 2

In the same manner as in Comparative Example 1 but using

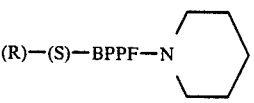

in place of (R)-(S)-BPPF-NMe$_2$ and no triethylamine, the reaction and post-treamtment were carried out to obtain (S)-2-(4-chlorophenyl)-3-methylbutyric acid (211 mg).

| Conversion: | 92% |
|---|---|
| Selectivity: | >98% |
| Optical yield | 25.8% (+isomer) |

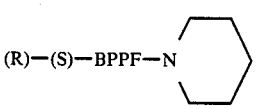

has a chemical structure of the formula:

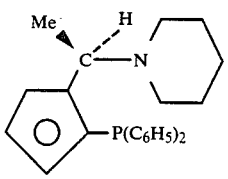

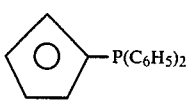

COMPARATIVE EXAMPLE 3

In the same manner as in Comparative Example 1 but using

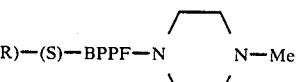

in place of (R)-(S)-BPPF-NMe₂ and no triethylamine, the reaction and post-treatment were carried out to obtain (S)-2-(4-chlorophenyl)-3-methylbutyric acid (212 mg).

| Conversion: | 99% |
|---|---|
| Selectivity: | >98% |
| Optical yield | 27.2% (+isomer) |

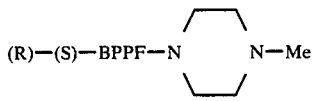

has a chemical structure of the formula:

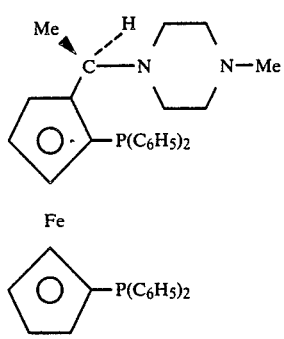

EXAMPLE 24

Rh₂(2,5-norbornadiene)₂Cl₂ (2.3 mg, 0.005 mmol), R(+)-2,2'-bis(diphenylphosphino)-1,1'-binaphthyl (7.8 mg, 0.0125 mmol), AgBF₄ (1.9 mg, 0.01 mmol) and triethylamine (5.1 mg, 0.05 mmol) were dissolved in methanol (15 ml) in a 35 ml autoclave. To the resulting solution, 2-(4-chlorophenyl)-3-methylcrotonic acid (0.42 g, 2 mmol) was dissolved. After replacing the autoclave interior with hydrogen gas three times, hydrogen gas was injected to pressurize the autoclave to 50 kg/cm², and the solution was stirred for 4 hours at 80° C.

After the reaction was completed, the catalyst was filtered off and the reaction mixture was concentrated to obtain S-2-(4-chlorophenyl)-3-methylbutyric acid (0.42 g).

| Conversion: | >98% |
|---|---|
| Selectivity: | >98% |
| Optical yield | 69% (+isomer) |

EXAMPLES 25 and 26

In the same manner as in Example 24 but pressurizing the autoclave to pressure as shown in Table 3, the reaction and post-treatment were carried out to obtain S-2-(4-chlorophenyl)-3-methylbutyric acid. The results are shown in Table 3.

TABLE 3

| Example No. | 25 | 26 |
|---|---|---|
| Hydrogen pressure (kg/cm²) | 30 | 100 |
| Conversion (%) | 91 | >98 |
| Selectivity (%) | >98 | >98 |

TABLE 3-continued

| Example No. | 25 | 26 |
|---|---|---|
| Optical yield (%) (+isomer) | 69 | 70.5 |

EXAMPLE 27

In the same manner as in Example 24 but using S(−)-2,2'-bis(diphenylphosphino)-1,1'-binaphthyl in place of R(+)-2,2'-bis(diphenylphosphino)-1,1'-binaphthyl, the reaction and post-treatment were carried out to obtain (R)-2-(4-chlorophenyl)-3-methylbutyric acid.

| Conversion: | >98% |
|---|---|
| Selectivity: | >98% |
| Optical yield | 69% (−isomer) |

EXAMPLE 28

Rh₂(1,5-cyclooctadiene)₂Cl₂ (2.5 mg, 0.005 mmol), R(+)-2,2'-bis(diphenylphosphino)-1,1'-binaphthyl (7.8 mg, 0.0125 mmol), AgBF₄ (1.9 mg, 0.01 mmol) and triethylamine (10.2 mg, 0.10 mmol) were dissolved in methanol (15 ml) in a 35 ml autoclave. To the resulting solution, 2-(4-chlorophenyl)-3-methylcrotonic acid (0.42 g, 2 mmol) was dissolved. After replacing the autoclave interior with hydrogen gas three times, hydrogen gas was injected to pressurize the autoclave to 50 kg/cm², and the solution was stirred for 4 hours at 80° C.

After the reaction was completed, the catalyst was filtered off and the reaction mixture was concentrated to obtain S-2-(4-chlorophenyl)-3-methylbutyric acid (0.42 g).

| Conversion: | >98% |
|---|---|
| Selectivity: | >98% |
| Optical yield | 65.0% (+isomer) |

EXAMPLE 29

Ru(2,5-norbornadiene)Cl₂ (2.6 mg, 0.01 mmol), S(−)-2,2'-bis(diphenylphosphino)-1,1'-binaphthyl (7.8 mg, 0.0125 mmol) and triethylamine (5.1 mg, 0.05 mmol) were dissolved in methanol (15 ml) in a 35 ml autoclave. To the resulting solution, 2-(4-chlorophenyl)-3-methylcrotonic acid (0.42 g, 2 mmol) was dissolved. After replacing the autoclave interior with hydrogen gas three times, hydrogen gas was injected to pressurize the autoclave to 50 kg/cm², and the solution was stirred for 4 hours at 80° C.

After the reaction was completed, the catalyst was filtered off and the reaction mixture was concentrated to obtain R-2-(4-chlorophenyl)-3-methylbutyric acid (0.42 g).

| Conversion: | >98% |
|---|---|
| Selectivity: | >98% |
| Optical yield | 68% (−isomer) |

EXAMPLE 30

Rh₂(NBD)₂Cl₂ (2.3 mg, 0.005 mmol); AgBF₄ (1.9 mg, 0.01 mmol), S(−)-cyclohexyl-BINAP (8.1 mg, 0.0125 mmol) and triethylamine (5.1 mg, 0.05 mmol) were dissolved in methanol (15 ml) in a 35 ml autoclave. To the resulting solution, 2-(4-chlorophenyl)-3-methylcrotonic acid (0.42 g, 2 mmol) was added and dissolved. After the interior space of the autoclave was replaced with hydrogen gas, hydrogen gas was injected to pressurize the autoclave to 50 kg/cm², and the solution was stirred for 24 hours at room temperature.

After hydrogen gas was purged, methanol was evaporated off. The residual mixture was extracted with an alkali, precipitated with an acid and extracted with ether followed by concentration to obtain (S)-2-(4-chlorophenyl)-3-methylbutyric acid (0.42 g).

| Conversion: | 100% |
|---|---|
| Selectivity: | >98% |
| Optical yield | 76.5% (+isomer) |

EXAMPLE 31

Rh₂(NBD)₂Cl₂ (2.3 mg, 0.005 mmol), AgBF₄ (1.9 mg, 0.01 mmol), R(+)-p-tolyl-BINAP (8.5 mg, 0.0125 mmol) and triethylamine (5.1 mg, 0.05 mmol) were dissolved in methanol (15 ml) in a 35 ml autoclave. To the resulting solution, 2-(4-chlorophenyl)-3-methylcrotonic acid (0.42 g, 2 mmol) was added and dissolved. After the interior space of the autoclave was replaced with hydrogen gas, hydrogen gas was injected to pressurize the autoclave to 50 kg/cm², and the solution was stirred for 4 hours at 80° C.

After the autoclave was cooled and hydrogen gas was purged, methanol was evaporated off. The residual mixture was extracted with an alkali, precipitated with an acid and extracted with ether followed by concentration to obtain (S)-2-(4-chlorophenyl)-3-methylbutyric acid (0.42 g).

| Conversion: | 95% |
|---|---|
| Selectivity: | >98% |
| Optical yield | 63.0% (+isomer) |

EXAMPLE 32

In the same manner as in Example 30 but using R(+)-p-CH₃O-BINAP (9.3 mg, 0.0125 mmol) in place of R(+)-p-tolyl-BINAP, the reaction and post-treatment were carried out to obtain (S)-2-(4-chlorophenyl)-3-methylbutyric acid (0.42 g).

| Conversion: | 95% |
|---|---|
| Selectivity: | >98% |
| Optical yield | 57.9% (+isomer) |

COMPARATIVE EXAMPLE 4

According to the process described in U.S. Pat. No. 4,409,397, Rh₂(1,5-norbornadiene)₂Cl₂ (2.3 mg, 0.005 mmol), (R)-(S)-PPFA (5.5 mg, 0.0125 mmol), AgBF₄ (1.9 mg, 0.01 mmol) and triethylamine (5.1 mg, 0.005 mmol) were dissolved in methanol (7.5 ml) in a 35 ml autoclave. To the resulting solution, 2-(4-chlorophenyl)-3-methylcrotonic acid (211 mg, 1 mmol) was added and dissolved. After replacing the autoclave interior with hydrogen gas three times, hydrogen gas was injected to pressurize the autoclave to 50 kg/cm², and the solution was stirred for 4 hours at 80° C.

After the reaction was completed, the catalyst was filtered off and the reaction mixture was concentrated to obtain (S)-2-(4-chlorophenyl)-3-methylbutyric acid (211 mg).

| Conversion: | 10% |
|---|---|
| Selectivity: | >98% |
| Optical yield | 3% (+isomer) |

(R)-(S)-PPFA has a chemical structure of the formula:

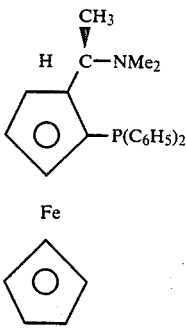

What is claimed is:

1. A process for preparing an optically active arylacetic acid derivative of the formula:

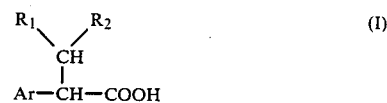

wherein R₁ and R₂ are the same or differnet and are a hydrogen atom, a lower alkyl group or a phenyl group; and Ar is a group of the formula:

 or a group of the formula:

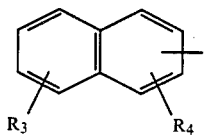

wherein R₃ and R₄ are the same or different and are each a hydrogen atom, a halogen atom, a lower alkyl group, a lower alkoxy group, a difluoromethoxy group, trifluoromethyl group or a phenyl group, which comprises asymmetrically reducing an ethylenically unsaturated compound of the formula:

wherein R₁, R₂ and Ar are the same as defined above with hydrogen in the presence of a metal catalyst modified with a ligand selected from the group consisting of:

an optically active metallocenyl phosphine derivative of the formula:

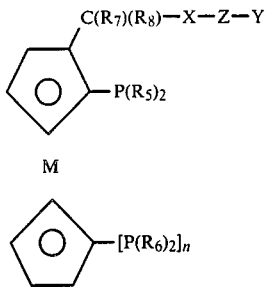

wherein $R_5$ and $R_6$ are the same or different and are each a lower alkyl group, a $C_5$-$C_8$ cycloalkyl group, an aryl group or a $C_5$-$C_6$ heterocyclic group; $R_7$ and $R_8$ are the same or different and are each a hydrogen atom or a lower alkyl group; X is a methylene group, an oxygen atom or a group of the formula: $-NR_9$ wherein $R_9$ is a hydrogen atom or a lower alkyl group; Z is an alkylene group, or a group of the formula:

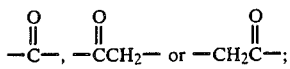

Y is a group of the formula: $-OR_{10}$ or $-N{<}R_{11}\,R_{12}$ wherein $R_{10}$, $R_{11}$ and $R_{12}$ are the same or different and are each a hydrogen atom or a lower alkyl group or $R_{11}$ and $R_{12}$ together form a heterocyclic group containing the nitrogen atom to which they are bonded and optionally an additional oxygen or nitrogen atom; M is Fe, Ru or Os; and n is 0 (zero) or 1 (one) and an optically active binaphthyl derivative of the formula:

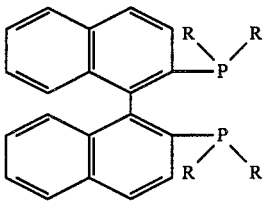

wherein R is a phenyl group, a p-tolyl group, a p-methoxy-phenyl group or a cyclohexyl group.

2. The process according to claim 1, wherein the metal in the catalyst is one selected from the group consisting of rhodium, iridium and ruthenium.

3. The process according to claim 1, wherein the metal catalyst is modified with the optically active metallocenyl phosphine derivative (III).

4. The process according to claim 3, wherein M in the optically active metallocenyl phosphine derivative (III) is an iron atom.

5. The process according to claim 3, wherein the metal catalyst is modified with the optically active ferrocenyl phosphine derivative (III) wherein M is an iron atom, $R_5$ and $R_6$ are independently a t-butyl group, a cyclohexyl group or a phenyl group; $R_7$ is a hydrogen atom; $R_8$ is a methyl group; X is NMe; Z is a methylene group, an ethylene group, a trimethylene group, a tetra-methylene group or a carbonyl group; Y is $-N(R_{11})(R_{12})$ wherein $R_{11}$ and $R_{12}$ are independently a lower alkyl group or together form a heterocyclic group containing the nitrogen atom to which they are bonded and optionally additional oxygen atom or nitrogen atom, n is 0 or 1.

6. The process according to claim 5, wherein the optically active ferrocenyl phosphine derivative is optically active N-methyl-[2-(1-piperidine)ethyl]-1-[1',2-bis(diphenylphosphino)-ferrocenyl]ethylamine.

7. The process according to claim 5, wherein the optically active ferrocenyl phosphine derivative is optically active N-methyl-[2-(diethylamino)ethyl]-1-[1',2-bis(diphenylphosphino)ferrocenyl]ethylamine.

8. The process according to claim 5, wherein the optically active ferrocenyl phosphine derivative is optically active N-methyl-[2-(hexahydro-1H-azepin-1-yl)ethyl]-1-[1',2-bis(diphenylphosphino)ferrocenyl]ethylamine.

9. The process according to claim 1, wherein the metal catalyst is modified with the optically active binaphthyl derivative (IV).

10. The process according to claim 1, wherein the lower alkyl group for $R_1$ through $R_{12}$ is a member selected from the group consisting of methyl, ehtyl, propyl, isopropyl, butyl, sec-butyl, tert-butyl, isobutyl, isamyl, pentyl, and hexyl.

11. The process according to claim 1, wherein the lower alkoxy group of $R_3$ and $R_4$ is a member selected from the group consisting of methoxy, ethyoxy, propoxy, isopropoxy, butoxy, isobutoxy, pentyloxy, and hexyloxy.

12. The process according to claim 1, wherein the alkylene group of Z is a member selected from the group consisting of methylene, ethylene, trimethylene, tetramethylene, pentamethylene, hexamethylene, ethylethylene, and methyltetramethylene.

13. The process according to claim 1, wherein the hetereocyclic group formed by $R_{11}$ and $R_{12}$ is a member selected from the group consisting of pyrrolidinyl, piperidino, morpholino, piperazyl, hexahydro-1H-azepinyl and 4-methylpiperazyl.

14. The process according to claim 1, wherein the ethylenically unsaturated compound of the formula (II) is a member selected from the group consisting of 2-phenyl-3-methylcrotonic acid, 2-(4-chloro-phenyl)-3-methylcrotonic acid, 2-(4-methoxyphenyl)-3-methylcrotonic acid, 2-(4-difluoromethoxyphenyl)-3-methylcrotonic acid, 2-(4-isobutylphenyl)acrylic acid, 2-(6-methoxynaphthyl-2)acrylic acid, 2-phenylacrylic acid, 2-phenyl-3-ethyl-pentenoic acid, 2-(4-chlorophenyl)-3-ethylpentenoic acid, 2-(2-naphthyl)-3-methylcrotonic acid, 2-phenyl-3-methyl-cinnamic acid, and 2-phenyl-3-methyl-2-pentenoic acid.

15. The process according to claim 1, wherein the catalyst is used in an amount of 0.001 to 10% by mole based on the amount of the ethylenically unsaturated compound (II).

16. The process according to claim 1, wherein the solvent is used in amount of 1 to 500 parts by weight per part by weight of the ethylenically unsaturated compound (II).

17. The process according to claim 1, wherein the reaction temperature is from 0° to 150° C.

* * * * *